(12) United States Patent
Dubois

(10) Patent No.: US 9,259,707 B2
(45) Date of Patent: Feb. 16, 2016

(54) CATALYTIC REACTION WITH REVERSE-FLOW REGENERATION

(71) Applicant: Jean-Luc Dubois, Millery (FR)

(72) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/405,426

(22) PCT Filed: Jun. 6, 2013

(86) PCT No.: PCT/FR2013/051296
§ 371 (c)(1),
(2) Date: Dec. 4, 2014

(87) PCT Pub. No.: WO2013/182818
PCT Pub. Date: Dec. 12, 2013

(65) Prior Publication Data
US 2015/0141703 A1    May 21, 2015

(30) Foreign Application Priority Data

Jun. 8, 2012 (FR) ..................................... 12 55368

(51) Int. Cl.
| | | |
|---|---|---|
| C07C 45/52 | (2006.01) | |
| C07C 17/37 | (2006.01) | |
| C07C 51/00 | (2006.01) | |
| B01J 19/24 | (2006.01) | |
| B01J 8/06 | (2006.01) | |
| B01J 8/02 | (2006.01) | |

(52) U.S. Cl.
CPC ........ *B01J 19/24* (2013.01); *B01J 8/025* (2013.01); *B01J 8/0278* (2013.01); *B01J 8/065* (2013.01); *B01J 19/249* (2013.01); *C07C 45/52* (2013.01); *B01J 2219/247* (2013.01)

(58) Field of Classification Search
CPC ........ C07C 45/52; C07C 17/37; C07C 51/377
USPC .................. 568/486; 570/155, 163; 562/599
See application file for complete search history.

(56) References Cited

U.S. PATENT DOCUMENTS 4,461,745 A * 7/1984 Ahlstrom, Jr. ................ 422/652

FOREIGN PATENT DOCUMENTS

| DE | 102 39 547 A1 | 3/2004 |
|---|---|---|
| EP | 0 154 674 A1 | 9/1985 |
| WO | WO2006/087083 A2 * | 8/2006 |
| WO | WO2010/123154 A2 * | 10/2010 |

OTHER PUBLICATIONS

Kolios, G., et al., "Autothermal Fixed-Bed Reactor Concepts", *Chemical Engineering Science*, vol. 55 (Dec. 2000), pp. 5945-5967.
International Search Report for PCT/FR2013/051296, mailed Sep. 25 2013.

* cited by examiner

*Primary Examiner* — Sikarl Witherspoon
(74) *Attorney, Agent, or Firm* — Brinks, Gilson & Lione

(57) ABSTRACT

The invention concerns a chemical reaction process performed in a reaction chamber (1) which contains a catalyst bed, the reaction chamber (1) comprising a first end (2) and a second end (3), opposite the first end (2), the process involving alternately: a reaction phase, in which a reaction flow passes through the reaction chamber (1) from its first end (2) towards its second end (3); and a catalyst-regeneration phase, in which a regeneration flow passes through the reaction chamber (1) from its second end (3) towards its first end (2). The reaction chamber (1) preferably consists of a plurality of separate reaction compartments containing a catalyst bed and a heat-exchange system for exchanging heat therebetween.

11 Claims, 1 Drawing Sheet

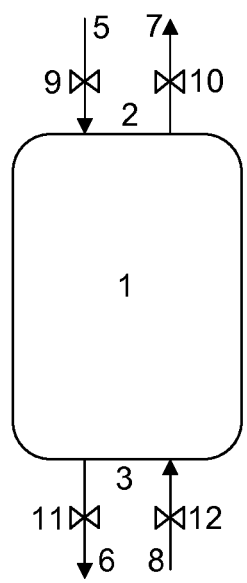

CATALYTIC REACTION WITH REVERSE-FLOW REGENERATION

This application is a National Stage application of International Application No. PCT/FR2013/051296, filed Jun. 6, 2013. This application also claims priority under 35 U.S.C. §119 to French Application No. 1255368, filed Jun. 8, 2012.

FIELD OF THE INVENTION

The present invention relates to a chemical reaction process comprising alternate reaction and regeneration phases. The invention also relates to the use of a chemical reactor suitable for the implementation of this process.

TECHNICAL BACKGROUND

The use of chemical reactions, especially involving a heterogeneous catalyst, in fixed bed reactors is known. In processes of this type, control of the heat absorbed or emitted represents a critical aspect.

For example, in exothermic reactions such as combustion reactions, a hot front has a tendency to form in the reactor when the reaction starts, and this hot front has a tendency thereafter to move in the bed of the reactor in the flow direction, until optionally exhibiting a risk of leaving the bed.

In order to resolve this problem, reverse-flow reactors have been developed. The principle of these systems is based on a reversal of the reaction flow that makes it possible to keep the hot front in the bed of the reactor during the reaction.

Documents WO 02/051965 and U.S. Pat. No. 5,710,356 provide examples of such symmetrical systems, in which the same flow passes through the reactor alternately in one direction and in the opposite direction.

Document U.S. Pat. No. 7,763,174 describes a variant in which adsorbent beds are placed on each side of the catalyst bed.

Still with an objective of optimizing heat transfers, asymmetric reverse-flow reaction processes have also been proposed, in order to enable the thermal coupling of an exothermic reaction and of an endothermic reaction. For example, a first flow direction may be used in order to carry out the combustion of methane (injection of methane and air), whilst the reverse flow direction may be used to carry out methane reforming (injection of methane and water). The first reaction is intended to heat the catalyst bed to a sufficient level to enable the second, endothermic, methane reforming reaction. Document US 2004/0170559 provides an illustration of such an asymmetrical process.

In the reverse-flow reactor systems described above, no specific measure is provided for the regeneration of the catalyst, once the latter is deactivated.

Document DE 10239547 illustrates another example of a thermal coupling of an endothermic reaction and of an exothermic reaction, this time by combining methane reforming with catalyst regeneration. According to this process, steam methane reforming is carried out at 400° K in a reactor comprising distributors for the injection of a supplementary flow introduced by supply pipes integrated into the reactor. During the regeneration, the flow direction is reversed and the internal distributors are supplied with a fuel in order to reach a regeneration temperature of 1000° K.

The process performed in document U.S. Pat. No. 4,461,745 consists in simultaneously carrying out a reaction and a regeneration, each in one half of a reaction chamber, then in reversing these 2 phases, the stream resulting from the regeneration step always being mixed in the reaction chamber with the reaction stream in order to supply the reaction phase zone.

Within the context of catalytic reactions for fluorination or for production of acrylic compounds that are carried out in a fixed bed, the catalyst is deactivated in particular by elimination of coke thereon. The regeneration of the catalyst may be carried out by combustion of the coke, by injecting a stream rich in oxygen or in air into the reactor.

However, the proportion of coke in the reactor is not homogeneous: there is, in principle, more coke accumulated toward the inlet of the reactor than toward the outlet thereof. This poses a combustion control problem. For example, a hot front may appear, leading to a very high temperature differential, which is capable of degrading the catalyst.

There is therefore a need to achieve a better control of the regeneration phase of processes of this type, in particular by avoiding the risks of degradation of the catalyst.

SUMMARY OF THE INVENTION

The invention relates firstly to a chemical reaction process performed in a reaction chamber containing a catalyst bed, the reaction chamber comprising a first end and a second end opposite the first end, the process alternately comprising:
- a reaction phase, comprising the passage of a reaction stream in the reaction chamber from its first end to its second end; and
- a catalyst regeneration phase, comprising the passage of a regeneration stream in the reaction chamber from its second end to its first end.

According to the invention, the reaction chamber consists of a plurality of separate reaction compartments containing a catalyst bed and comprising a system for heat exchange therebetween, in order to carry out the heat exchanges effectively.

The reaction phase and the regeneration phase are two separate phases produced on one and same assembly of catalyst beds successively and alternately.

According to an embodiment, the regeneration stream comprises oxygen, and the regeneration phase of the catalyst comprises the combustion of coke deposited on the catalyst.

According to one embodiment, the chemical reaction process is:
- a process for dehydrating glycerol to acrolein; or
- a process for dehydrating lactic acid or ammonium lactate to acrylic acid; or
- a process for dehydrating 3-hydroxypropionic acid or the ammonium salt thereof to acrylic acid; or
- a process for dehydrating 2-hydroxyisobutyric acid or 3-hydroxyisobutyric acid or the corresponding ammonium salts thereof to methacrylic acid; or
- a process for converting a chloro compound to a fluoro compound, preferably a process for preparing a hydrofluoroolefin or a hydrofluorocarbon, especially a process for preparing a fluoropropene, and most particularly preferably a process for preparing 2,3,3,3-tetrafluoropropene; or
- a selective oxidation process such as the oxidation of methanol to formaldehyde or to dimethoxymethane; the oxidation of ethanol to acetaldehyde or diethoxyethane; the oxidation of ortho-xylene or naphthalene to phthalic anhydride; the oxidation of benzene, butene, butanol or butane to maleic anhydride; the oxidation of propylene to acrolein; the oxidation of isobutene or tert-butanol to methacrolein.

According to one embodiment, the process is an exothermic reaction process.

According to one embodiment, the reaction phase has a duration of greater than or equal to 15 minutes, preferably greater than or equal to 1 hour or greater than or equal to 15 hours; and/or the regeneration phase has a duration of greater than or equal to 15 minutes and preferably greater than or equal to 5 hours.

According to an embodiment, the reaction phase and the regeneration phase have different durations, in particular the duration of the regeneration phase is shorter than the duration of the reaction phase.

According to one embodiment, the reaction phase and the regeneration phase have predetermined durations; or the duration of the reaction phase and/or the duration of the regeneration phase depend on the measurement of a parameter such as a temperature in the reactor or the content of a compound in a stream leaving the reactor.

The invention also relates to the use of a reactor suitable for performing a process alternately comprising a reaction phase and regeneration phase as defined above. This reactor is a chemical reactor comprising:
- a reaction chamber containing a catalyst bed, the reaction chamber comprising a first end and a second end opposite the first end;
- a reaction stream supply pipe connected to the inlet of the reaction chamber at its first end;
- a reaction stream withdrawal pipe connected to the outlet of the reaction chamber at its second end;
- a regeneration stream supply pipe connected to the inlet of the reaction chamber at its second end;
- a regeneration stream withdrawal pipe connected to the outlet of the reaction chamber at its first end;
- switching means suitable for alternately allowing the passage of a reaction stream in the reaction chamber from the reaction stream supply pipe to the reaction stream withdrawal pipe, and the passage of a regeneration stream from the regeneration stream supply pipe to the regeneration stream withdrawal pipe.

According to one preferred embodiment, the reaction chamber comprises a plurality of individual reaction compartments, the reactor preferably being a plate reactor or a multitubular reactor.

The present invention makes it possible to overcome the drawbacks of the prior art. More particularly, it makes it possible to arrive at a better control of the (in situ) regeneration phase of the catalyst, within the context of fixed-bed chemical reactions, especially while avoiding the risks of degradation of the catalyst.

This is accomplished owing to the reversal of the flow direction in the reactor between the reaction phase on the one hand and the regeneration phase on the other hand.

According to certain particular embodiments, the invention also has one or preferably several of the advantageous characteristics listed below:

The reversal of the flow direction during the regeneration makes it possible to start the combustion of the coke in the zone of the reactor that is relatively the least laden with coke. In this way, an excessively high temperature gradient that risks modifying the crystalline structure of the catalyst, and thus degrading it, is avoided.

A regeneration without reversal of the flow direction leads to a preferential combustion of the coke at the inlet (due to the appearance of the hot front at the inlet, and due to the lower concentration of oxygen at the outlet). Consequently, the reversal of the flow direction during the regeneration provided by the invention makes it possible to reduce the amount of coke in the reactor more homogeneously along this reactor. Such a more homogeneous reduction of the amount of coke may furthermore result, after the regeneration, in a larger proportion of coke being retained at the inlet of the reactor than at the outlet (with respect to the direction of the reaction stream), just like before the regeneration. The retention of this coke differential between the inlet and the outlet makes it possible to avoid having an excessively reactive catalyst bed volume at the inlet which may result in side reactions. In other words, the invention enables a better control of the activity of the catalyst.

During the reaction phase, just like during the regeneration phase, there may be a partial sublimation of metals from the catalyst bed, and deposition of these metals downstream. The reversal of the flow direction between the reaction and the regeneration makes it possible to keep these metals in the catalyst bed and prevent them from escaping outside of the reactor.

A regeneration without reversal of the flow direction may lead to a reactor inlet that is colder than the outlet at the end of the regeneration step (due to the movement of the hot front during the regeneration). It is therefore necessary to reheat the catalyst bed in order to start the reaction. Such a measure is not necessary, or is less necessary, if the flow direction is reversed during the regeneration, since it is then the inlet of the reactor which is hotter than the outlet at the end of the regeneration phase.

BRIEF DESCRIPTION OF THE FIGURES

FIG. 1 schematically represents a chemical reactor according to the invention.

DESCRIPTION OF EMBODIMENTS OF THE INVENTION

The invention is now described in greater detail and non-limitingly in the description that follows.

By referring to FIG. 1, generally, the reactor according to invention comprises a reaction chamber 1, which comprises a first end 2 and a second end 3 opposite the first. A fixed catalyst bed is placed in the reaction chamber 1.

For example, the reactor may be of vertical type, in which case the first end 2 may be located at the top of the reaction chamber 1, and the second end 3 may be located at the bottom of the reaction chamber 1, as illustrated, but the reverse configuration is also possible. The reactor may also be of horizontal type.

The reactor comprises a reaction stream supply pipe 5, which is connected to the inlet of the reaction chamber 1 at its first end 2, and a reaction stream withdrawal pipe 6 connected to the outlet of the reaction chamber 1 at its second end 3.

The reactor furthermore comprises a regeneration stream supply pipe 8 connected to the inlet of the reaction chamber 1 at its second end 3, and a regeneration stream withdrawal pipe 7 connected to the outlet of the reaction chamber 1 at its first end 2.

It is optionally possible to provide, for each of the above pipes, a single pipe, but also several pipes in parallel. Subsequently, the example of single pipes is taken.

The reaction chamber 1 may be a single reaction compartment, for example of cylindrical type with a circular cross section (adiabatic reactor). But preferably according to invention, the reaction chamber 1 comprises a plurality of separate reaction compartments, each containing its own fixed catalyst bed. In this case, the reaction compartments are positioned in parallel, that is to say that distribution systems (not represented) make it possible to distribute a stream from the reaction stream supply pipe 5 to all of the reaction compartments, to distribute a stream from the regeneration stream supply pipe 8 to all of the reaction compartments, to collect a stream from all of the reaction compartments to the reaction stream withdrawal pipe 6 and to collect a stream from all of the reaction compartments to the regeneration stream withdrawal pipe 7.

The reaction compartments may for example be tubular (cylindrical with a circular cross section) compartments, in the case of a multi-tubular reactor. They may also be parallelepipedal compartments, in the case of a plate reactor.

A heat exchange system (known per se) is provided between the reaction compartments in order to enable heat exchanges.

Each reaction compartment comprises a catalyst bed. The catalyst may be in the form of solid particles (beads, grains or powder) or in the form of a porous monolith or blocks of porous monolith.

The catalyst bed may also comprise two parts, each comprising a different catalyst. In this case, it may be advantageous to provide a vertical reactor, the catalyst with the shorter service life being positioned above the catalyst with longer service life, in order to make the replacement thereof easier. In this case, the reaction is carried out by injecting a stream from the bottom upwards.

The reactor operates alternately according to two phases, namely a reaction phase, during which the desired chemical reaction takes place in the reaction chamber 1, and during which the catalyst has a tendency to be gradually deactivated; and a regeneration mode, during which the at least partially deactivated catalyst is regenerated.

Within the context of the present application, the expression "reaction stream" is understood in the broad sense and denotes a stream that crosses the reaction chamber 1 from the first end 2 to the second end 3 and enables the reaction to be performed, it being understood that the composition of the reaction stream varies between the inlet and the outlet of the reactor.

Similarly, the expression "regeneration stream" denotes a stream that crosses the reaction chamber 1 from the second end 3 to the first end 2 and enables the regeneration of the catalyst to be carried out, it being understood that the composition of the regeneration stream varies between the inlet and the outlet of the reactor.

In the reaction phase, it is the reaction stream which crosses the reaction chamber 1. At the inlet, this reaction stream comprises the reactants necessary for performing the reaction, and at the outlet it comprises, at least partly, the products of the reaction.

In the regeneration phase, it is the regeneration stream which crosses the reaction chamber 1. At the inlet, this regeneration stream comprises one or more compounds capable of regenerating the catalyst, and at the outlet it comprises the residues of the regeneration.

Each of the streams may be of liquid or gaseous or mixed type.

The reaction stream supply pipe 5 is advantageously connected to a reaction stream reservoir, and the regeneration stream supply pipe 8 is advantageously connected to a regeneration stream reservoir.

A system of valves 9, 10, 11, 12 makes it possible to close and open each of the pipes mentioned above, so as to operate the reactor alternately in the reaction phase and in the regeneration phase, by virtue of switching means that are not represented.

The reaction and regeneration phases may have predetermined durations, as a function of known deactivation and regeneration profiles of the catalyst. These are preferably different durations, namely a shorter regeneration duration than the duration of the reaction phase. Alternatively, passing from the reaction phase to the regeneration phase and vice versa may be carried out as a function of a measured parameter, such as a temperature profile, or the concentration of a substance in the outlet stream (for example the concentration of a reaction product in the reaction stream at the outlet, or the concentration of oxygen or of carbon monoxide or of carbon dioxide in the regeneration stream at the outlet).

According to one embodiment, the duration of the reaction phase is greater than or equal to 15 minutes, preferably greater than or equal to 1 hour, or to 3 hours, or to 5 hours, or to 10 hours, or to 15 hours.

According to one embodiment, the duration of the regeneration phase is greater than or equal to 15 minutes, preferably greater than or equal to 1 hour, or to 3 hours, or to 5 hours.

According to certain embodiments, the duration of the reaction phase is less than or equal to 200 hours, or less than or equal to 100 hours, or less than or equal to 50 hours, or less than or equal to 25 hours.

According to certain embodiments, the duration of the regeneration phase is less than or equal to 200 hours, or less than or equal to 100 hours or less than or equal to 50 hours, or less than or equal to 25 hours, or less than or equal to 15 hours.

According to one embodiment, the regeneration of the catalyst is only partial during the regeneration phase (that is to say that the regeneration phase is interrupted before the regeneration of the catalyst is complete or virtually complete), thus for example a portion of the coke remains in the reactor at the inlet of the reaction zone, which makes it possible to optimize the duration of use of the reactor in the reaction phase, to minimize the duration in the regeneration phase, and to optimize the overall productivity.

The invention is, for example, carried out for the production of acrolein and/or acrylic acid of renewable origin, in particular the production of acrylic acid from glycerol, comprising a first step of dehydration of glycerol to give acrolein followed by a step of oxidation, in the gas phase, of the acrolein thus obtained; or in the production of acrylic acid by dehydration of 2-hydroxypropionic acid (lactic acid) or 3-hydroxypropionic acid and esters thereof or the corresponding ammonium salts.

The invention makes it possible in particular to carry out a process for the dehydration of glycerol to give acrolein. In this type of process, the glycerol is supplied in the form of an aqueous solution with a concentration of 20% to 95% by weight. The more concentrated the glycerol is, the greater the tendency of the catalyst to form coke, requiring frequent regenerations. According to the process described in application WO 2006/087083, the reaction is advantageously carried out in the presence of oxygen, the addition of oxygen to the glycerol dehydration reaction making it possible to prolong the service life of the catalyst and to space out the regenerations.

The reaction is typically carried out at a temperature of from 220° C. to 350° C. and preferably from 280° C. to 320° C.; and at a pressure that varies from atmospheric pressure to a few bar (for example 5 bar).

The catalysts that can be used for this reaction are acid catalysts, in particular having a Hammett acidity of less than +2, as described for example in documents EP 1 848 681, WO 2009/12855, WO 2009/044081 or WO 2010/046227. Many acid catalysts may be suitable for this reaction. Mention will be made of phosphated zirconias, tungstated zirconias, silica zirconias, titanium or tin oxides impregnated with tungstate or phosphotungstate or silicotungstate, phosphated aluminas or silicas, heteropolyacids or heteropolyacid salts, iron phosphates and iron phosphates comprising a promoter, titanium oxide catalysts impregnated with tungstate or phosphotungstate or silicotungstate and/or alkali metal salts of these compounds.

The invention also makes it possible to carry out a process for the dehydration of lactic acid or 3-hydroxypropionic acid (and the corresponding esters thereof) or the ammonium salts thereof, to give acrylic acid.

Lactic acid has a boiling point in the vicinity of 217° C. and 3-hydroxypropionic acid has a boiling point of 279° C. (calculated value). The flammability limits for lactic acid in air are 3.1% (lower limit) and 18% (upper limit). The methyl ester of lactic acid as a boiling point of 145° C., for flammability limits of 1.1% and 3.6% (which gives greater flexibility of use than for the acid). The methyl ester of 3-hydroxypropionic acid has a boiling point of 179° C. (180° C. as calculated value), the ethyl ester of lactic acid has a boiling point of 154° C., and flammability limits of 1.6% and 10.6%. The ethyl ester of 3-hydroxypropionic acid has a boiling point of 187.5° C.

For these reactions, use is made of a reactor configuration substantially identical to that for the dehydration of glycerol. The dehydration conditions are a temperature of 220° C. to 400° C., and preferably of 250° C. to 350° C., and a pressure of 0.5 to 5 bar.

The catalysts that may be suitable for these reactions are acid catalysts, having in particular a Hammett acidity of less than +2. The catalyst may be selected from natural or synthetic siliceous materials or acidic zeolites; mineral supports, such as oxides, covered with mono-, di-, tri- or polyacidic inorganic acids; oxides or mixed oxides or heteropolyacids or heteropolyacid salts containing in particular at least one element selected from the group comprising W, Mo and V. Mention may particularly be made, among mixed oxides, of those based on iron and on phosphorus and of those based on cesium, phosphorus and tungsten.

Other catalysts which may also be suitable for these reactions are obtained from phosphates and/or sulfates of alkali metals, alkaline earth metals and rare earth metals, and mixtures thereof. This group thus includes lanthanum phosphates and oxyphosphates, sodium phosphates, calcium phosphates, calcium sulfate, magnesium sulfate, and the corresponding hydrogenphosphates, aluminum phosphate, boron phosphate. All the abovementioned active materials can be impregnated or coated on any type of support, such as: alumina, titanium oxide, zirconium oxide or silica, but also the corresponding mixed oxides, and silicon carbide.

The lactic acid or 3-hydroxypropionic acid partial pressure is generally from 1% to 10% and preferably from 2% to 6%.

The invention also makes it possible to carry out a process for the dehydration of 2-hydroxyisobutyric acid or 3-hydroxyisobutyric acid or the corresponding ammonium salts thereof to methacrylic acid.

For this type of reaction, use is made of a reactor configuration substantially identical to that for the dehydration of glycerol. The dehydration conditions are a temperature of 200° C. to 400° C., and preferably of 250° C. to 350° C. and a pressure of 0.5 to 5 bar. The catalysts which may be suitable for this reaction are acid catalysts, having in particular a Hammett acidity of less than +2. The catalysts may be selected from natural or synthetic siliceous materials or acidic zeolites; inorganic supports, such as oxides, covered with mono-, di-, tri- or polyacidic inorganic acids; oxides or mixed oxides or heteropolyacids or heteropolyacid salts containing in particular at least one element selected from the group comprising W, Mo and V. Mention may particularly be made, among mixed oxides, of those based on iron and on phosphorus and of those based on cesium, phosphorus and tungsten.

Catalysts which may also be suitable for this reaction are obtained from phosphates and/or sulfates of alkali metals, alkaline earth metals and rare earth metals, and mixtures thereof. This group thus includes lanthanum phosphates and oxyphosphates, sodium phosphates, calcium phosphates, calcium sulfate, magnesium sulfate, and the corresponding hydrogenphosphates, aluminum phosphate, boron phosphate. All the abovementioned active materials can be impregnated or coated on any type of support, such as: alumina, titanium oxide, zirconium oxide or silica, but also the corresponding mixed oxides, and silicon carbide.

The (2- or 3-)hydroxyisobutyric acid partial pressure is generally from 1% to 10% and preferably from 2% to 6%.

Within the context of the above reactions, the catalyst undergoes deactivation, in particular by coking. This deactivation may however be delayed by addition of oxygen to the reaction stream.

Furthermore, in the regeneration phase, the catalyst is regenerated by introducing a regeneration stream based on oxygen or on air into the reaction chamber 1.

The regeneration conditions are adapted as a function of the type of the nature of the deactivation of the catalyst. For example, in the case of a deactivation by coking, there are various types of coke and in particular soft coke and hard coke.

Soft coke is rich in hydrogen and/or is eliminated at relatively low temperature, while hard coke is a coke that has evolved (matured) and is less rich in hydrogen and requires higher temperatures in order to initiate the combustion thereof. The regeneration in general requires a sufficient temperature, referred to as the ignition temperature, to be reached. The regeneration temperature is preferably greater than 300° C., more particularly greater than 325° C., and more preferably still greater than 350° C. The temperature may be adjusted during the regeneration in order to keep a temperature sufficient for maintaining the regeneration.

The pressure is preferably close to atmospheric pressure. It is essentially the oxygen partial pressure that determines the combustion kinetics. The oxygen partial pressure is preferably from 0.01 to 1 bar, and more particularly from 0.05 to 0.5 bar. The oxygen partial pressure may be adjusted during the regeneration, for example by adding steam, or else by adding nitrogen, or more simply by recycling gases resulting from the regeneration, that are richer in $CO_2$. The composition of the regeneration stream preferably comprises, amongst others, oxygen, nitrogen, steam, $CO_2$, carbon monoxide. Air may be used advantageously as a source of oxygen, but it is also possible to use other sources of oxygen such as enriched air or depleted air.

The invention also makes it possible to carry out selective oxidations, such as the oxidation of methanol to give formaldehyde or dimethoxymethane; the oxidation of ethanol to give acetaldehyde or diethoxyethane; the oxidation of orthoxylene or naphthalene to give phthalic anhydride; or the oxidation of benzene, butene, butanol or butane to give maleic anhydride.

In the case of the reactions for the oxidation of methanol to give formaldehyde or dimethoxymethane and for the oxidation of ethanol to give acetaldehyde or diethoxyethane, the catalysts which may be suitable are mixed oxides, such as iron molybdenum oxides or molybdenum oxides comprising metals chosen from bismuth, vanadium, tungsten, copper, nickel or cobalt. The operating conditions are a temperature of between 200° C. and 350° C., preferably between 250° C. and 300° C., and a pressure of between 1 and 5 bar. The alcohol partial pressure can vary within a wide range from 3% to 50% and preferably from 5% to 40%, according to the type of product desired. In the case where the aldehydes are the desired products, the alcohol partial pressure is between 3% and 10% and preferably between 5% and 9%. In the case where the acetals are the desired products, the alcohol partial pressure is between 10% and 50% and preferably between 20% and 40%.

In the case of the reactions for the oxidation of ortho-xylene and naphthalene to give phthalic anhydride, the catalysts selected preferably comprise vanadium and preferably supported vanadium oxide. The operating conditions are a pressure of 1 to 5 bar and reaction temperatures of 280° C. to 450° C.

In the case of the reactions for the oxidation of butane, butenes, butanol and benzene to give maleic anhydride, the catalysts which are suitable comprise vanadium, in the form of supported vanadium oxide or in the form of supported mixed vanadium/phosphorus oxide. The reaction temperatures are from 350° C. to 500° C. and the pressures are from 1 to 5 bar.

In the case of the reactions for the oxidation of propylene to give acrolein or of isobutene or tert-butanol to give methacrolein, the catalysts which are suitable consist predominantly of molybdenum and comprise elements chosen from (but not exclusively) the following elements: nickel, iron, cobalt, tungsten, potassium, bismuth, antimony or chromium. The reaction temperatures are between 320° C. and 450° C. The total pressures are between 1 and 5 bar. The hydrocarbon compound partial pressures are between 5% and 15% and the $O_2$/hydrocarbon compound ratio at the reactor inlet is between 0.5 and 4, preferably between 0.8 and 2, more preferably still between 1 and 1.8 and even more preferably still between 1.2 and 1.6.

In the case of the reactions for the oxidation of acrolein to give acrylic acid and of methacrolein to give methacrylic acid, the catalysts which are suitable consist predominantly of molybdenum and comprise elements chosen from the following elements (but not exclusively): vanadium, tungsten, copper, antimony, niobium, strontium, phosphorus or iron. The operating temperatures are between 250° C. and 350° C., for a total pressure of 1 to 5 bar. The aldehyde partial pressure is between 5% and 15% and the $O_2$/aldehyde ratio at the reactor inlet is between 0.3 and 1.2 and preferably between 0.5 and 1.

Other oxidation reactions which can be carried out according to the invention are:
  The production of acrylic acid from propylene and oxygen, the coproducts being acrolein, acetic acid, maleic acid, propionic acid, acetaldehyde and acetone, for example at a temperature of 300° C. to 400° C. and at a pressure of 1 to 3 bar.
  The production of ethylene oxide from ethylene and oxygen, the coproducts being acetaldehyde and formaldehyde, for example at a temperature of 230° C. to 290° C. and at a pressure of 10 to 30 bar.
  The production of 1,2-dichloroethane from ethylene, hydrochloric acid and oxygen, the coproducts being carbon monoxide, chloral and various chlorinated compounds, for example at a temperature of 220° C. to 300° C. and at a pressure of 2 to 6 bar.
  The production of terephthalic acid from p-xylene and oxygen, the coproducts being maleic anhydride, o-toluic acid and benzoic acid, for example at a temperature of 175° C. to 230° C. and at a pressure of 15 to 30 bar.

The reactor according to the invention may also be suitable for ammoxidation reactions involving ammonia/oxygen/inert gas/hydrocarbon compound mixtures. The hydrocarbon compounds which can be used comprise propylene, isobutene, acrolein, methacrolein but also aromatic compounds. The ammoxidation reactions are carried out at a temperature from 50° C. to 100° C. higher than the corresponding oxidation temperatures.

By way of example, it is possible to produce acrylonitrile (while coproducing acetonitrile, hydrocyanic acid and carbon monoxide) from propylene and/or propane, oxygen and ammonia, for example at a temperature of 400° C. to 500° C. and at a pressure of 1 to 4 bar.

For all of the above oxidation reactions, little or no coke is produced, and the cycle times are generally counted in months or even in years. The advantage of the invention is in this case mainly to compensate for the migration of catalytic species such as molybdenum, and also to reduce the pressure drop by restructuring the catalyst bed.

The invention also makes it possible to carry out a fluorination process, that is to say a process for the preparation of a fluorinated compound from a chlorinated compound. Preferably, the reaction is carried out by reacting the chlorinated compound with hydrogen fluoride (HF).

The chlorinated compound can be any molecule having at least one chlorine atom and the fluorinated compound can be any molecule having at least one fluorine atom.

Preferably, the chlorinated compound is a linear or branched (preferably linear) $C_2$ or $C_3$ or $C_4$ or $C_5$ alkane or alkene comprising one or more substituents chosen from F, Cl, I and Br (preferably from F and Cl), at least one of the substituents being Cl.

Preferably, the fluorinated compound is a linear or branched (preferably linear) $C_2$ or $C_3$ or $C_4$ or $C_5$ alkane or alkene comprising one or more substituents chosen from F, Cl, I and Br (preferably from F and Cl), at least one of the substituents being F.

More particularly preferably, the chlorinated compound is a $C_3$ alkane or alkene comprising one or more substituents chosen from F, Cl, I and Br (preferably from F and Cl), at least one of the substituents being Cl, and the fluorinated compound is a $C_3$ alkene comprising one or more substituents chosen from F, Cl, I and Br (preferably from F and Cl), at least one of the substituents being F.

Alternatively, the chlorinated compound can be a $C_4$ alkane or alkene comprising one or more substituents chosen from F, Cl, I and Br (preferably from F and Cl), at least one of the substituents being Cl, and the fluorinated compound is a $C_4$ alkene comprising one or more substituents chosen from F, Cl, I and Br (preferably from F and Cl), at least one of the substituents being F.

According to one embodiment, the fluorinated compound is a hydrofluoroolefin (and thus does not comprise a Cl substituent).

Preferably, during the reaction, at least one Cl substituent of the chlorinated compound is replaced by an F substituent.

The conversion of the chlorinated compound to the fluorinated compound comprises the direct conversion (in just one stage or according to just one combination of operating conditions) and the indirect conversion (in two or more than two stages or by using more than one combination of operating conditions).

The fluorination reactions more particularly preferred are the reactions:
  of 2-chloro-3,3,3-trifluoro-1-propene (HFCO-1233xf) to give 2,3,3,3-tetrafluoro-1-propene (HFO-1234yf);

of 1,1,1,2,3-pentachloropropane (HCC-240db) to give 2,3,3,3-tetrafluoro-1-propene (HFO-1234yf);
of 1,1,2,2,3-pentachloropropane (HCC-240aa) to give 2,3,3,3-tetrafluoro-1-propene (HFO-1234yf);
of 2,3-dichloro-1,1,1-trifluoropropane (HCFC-243db) to give 2,3,3,3-tetrafluoro-1-propene (HFO-1234yf);
of 1,1,2,3-tetrachloro-1-propene (HCO-1230xa) to give 2,3,3,3-tetrafluoro-1-propene (HFO-1234yf);
of 2,3,3,3-tetrachloro-1-propene (HCO-1230xf) to give 2,3,3,3-tetrafluoro-1-propene (HFO-1234yf);
of 1,1,1,2,3-pentachloropropane (HCC-240db) to give 2-chloro-3,3,3-trifluoro-1-propene (HFCO-1233xf);
of 1,1,2,2,3-pentachloropropane (HCC-240aa) to give 2-chloro-3,3,3-trifluoro-1-propene (HFCO-1233xf);
of 2,3-dichloro-1,1,1-trifluoropropane (HCFC-243db) to give 2-chloro-3,3,3-trifluoro-1-propene (HFCO-1233xf);
of 1,1,2,3 tetrachloro-1-propene (HCO-1230xa) to give 2-chloro-3,3,3-trifluoro-1-propene (HFCO-1233xf);
of 2,3,3,3 tetrachloro-1-propene (HCO-1230xf) to give 2-chloro-3,3,3-trifluoro-1-propene (HFCO-1233xf).

The fluorination reaction can be carried out with an HF molar ratio typically of 3:1 to 150:1, with a contact time of 6 to 100 s and at a pressure from atmospheric pressure to 20 bar. The temperature of the reaction can be from 200° C. to 450° C.

A specific example of the process which makes it possible to prepare HFO-1234yf from HFCO-1233xf occurs in the document WO 2010/123154. This process can be carried out with the reactor according to the invention.

Furthermore, the reaction may be a dehydrohalogenation reaction, comprising the formation of a (preferably halogenated, and more particularly fluorinated) unsaturated compound from a halogenated (especially chlorinated and/or fluorinated) saturated compound, and involving the elimination of a molecule of HCl or HF type.

As examples of dehydrohalogenation, mention may be made of those resulting in 2,3,3,3-tetrafluoro-1-propene (HFO-1234yf), and especially the reactions:
of 2-chloro-1,1,1,2-tetrafluoropropane (HCFC-244bb) to give 2,3,3,3-tetrafluoro-1-propene (HFO-1234yf);
of 1,1,1,2,2-pentafluoropropane (HFC-245cb) to give 2,3,3,3-tetrafluoro-1-propene (HFO-1234yf);
of 1,1,1,2,3-pentafluoropropane (HFC-245eb) to give 2,3,3,3-tetrafluoro-1-propene (HFO-1234yf).

The catalyst used for the above reactions involving fluorinated compounds may or may not be supported.

It may be, for example, a metal catalyst, that is to say of the elemental metal, metal oxide, metal halide and/or metal salt type, in particular a transition metal oxide or a halide or oxyhalide of such a metal.

It may be, in particular, antimony halide, tin halide, thallium halide, iron halide and a combination thereof. Metal chlorides and fluorides are preferred, for example $SbCl_5$, $SbCl_3$, $SbF_5$, $SnCl_4$, $TiCl_4$, $FeCl_3$ and the combinations thereof.

Other appropriate catalysts are those based on chromium, such as chromium oxyfluoride, chromium oxides, such as $Cr_2O_3$ (optionally subjected to fluorination treatments), chromium fluorides and the combinations thereof.

Other possible catalysts are those based on aluminum (for example $AlF_3$, $Al_2O_3$ and aluminum oxyfluoride).

The catalyst can be chosen from fluorinated alumina, fluorinated titanium dioxide, fluorinated stainless steel, active charcoal and graphite.

It may be a mixture of chromium and magnesium (in the elemental, saline, oxide or halide form) or a mixture of chromium and another metal (in the elemental, saline, oxide or halide form).

It may also be a catalyst comprising a metal on a support.

The metal may be chosen from Groups 3, 4, 5, 6, 7, 8, 9 and 13 of the Periodic Table and may in particular be Al, Cr, Mn, Co, Ni, Zn, Ti, V, Ru, Rh, Pd, Os, Ir, Pt, Zr, Mo, Re, Sc, Y, La, Hf, Cu, Ag, Au, Ge, Sn, Pb or Mg, in particular Al, Cr, Mn, Ni or Co. It can be a lanthanide (metals 58 to 71 of the Periodic Table). The metal of the catalyst may be converted into metal derivatives during its activation or its regeneration, for example into oxide, halide (fluoride, bromide, chloride), oxyhalide or pseudohalide (cyanide, cyanate, thiocyanate).

The support may be chosen from aluminum, aluminum halides and aluminum oxyhalides, alumina, activated alumina, fluorinated alumina, aluminum fluoride, active charcoal (fluorinated or non-fluorinated) and graphite (optionally fluorinated).

The catalyst may be prepared, for example, by immersion of the support in a solution of soluble compound (for example, nitrate or chloride) of the metal, or alternatively the solution may be sprayed onto the support. The support may be dried and brought into contact with a halogenating agent in the vapor form (for example, hydrogen fluoride, hydrochloric acid, chlorofluorohydrocarbon, or else $SiF_4$, $CCl_3F$, $CCl_2F$, $CHF_3$ or $CCl_2FCClF_2$) with heating in order to partially or completely halogenate the support or the metal.

Examples of supported catalysts are $FeCl_3$ supported on carbon, alumina supported on carbon, aluminum fluoride supported on carbon, fluorinated alumina supported on carbon, magnesium fluoride supported on aluminum fluoride, more generally metals (elemental metals, metal oxides, metal halides and/or metal salts) supported on aluminum fluoride, metals supported on alumina, metals supported on carbon, or the mixtures of metals.

Other examples of supported catalysts are: a magnesium halide or a zinc halide supported on $Cr_2O_3$, a chromium(III) halide supported on carbon, a mixture of chromium and magnesium (in the elemental, oxide, halide or saline form) supported on graphite, a mixture of chromium and another metal (in the elemental, saline, oxide or halide form) supported on graphite or alumina or an aluminum halide, such as aluminum fluoride.

The total metal content of the supported catalyst is preferably from 0.1% to 20% by weight, for example from 0.1% to 10% by weight (with respect to the total weight of the catalyst).

A preferred embodiment uses a specific catalyst which is a supported mixed catalyst comprising both chromium and nickel. The Cr:Ni molar ratio (with respect to the metal elements) is generally from 0.5 to 5, for example from 0.7 to 2 and in particular in the vicinity of 1. The catalyst can comprise from 0.5% to 20% of chromium and from 0.5% to 20% of nickel by weight, preferably from 2% to 10% of each metal. Reference can be made, in this regard, to the document WO 2009/118628 and in particular to the description of the catalyst from p. 4, l. 30, to p. 7, l. 16.

An advantageous catalyst is a chromium-based catalyst comprising a chromium compound of the crystalline alpha-chromium oxide type, in which from 0.05% to 6% of the atoms approximately of the alpha-chromium oxide lattice are replaced with trivalent cobalt atoms (optionally treated with a fluorinating agent). Reference is made to the document US 2005/0228202 on this subject.

The catalyst may be subjected to a fluorination. As example of fluorination, it is possible to prepare a fluorinated alumina by bringing an alumina into contact with hydrogen fluoride with heating or by spraying an aqueous hydrogen fluoride solution at ambient temperature or by immersing an alumina in solution, and by then drying. The fluorination of the catalyst may or may not be carried out in the reactor according to the invention. The temperature during the fluorination is generally from 200° C. to 450° C.

The catalyst may optionally comprise a low content of one or more cocatalysts, such as Co, Zn, Mn, Mg, V, Mo, Te, Nb, Sb, Ta, P and Ni salts. A preferred cocatalyst is nickel. Another preferred cocatalyst is magnesium.

For example, an unsupported chromium-based catalyst may optionally comprise a low content of one or more cocatalysts chosen from cobalt, nickel, zinc or manganese and be prepared by processes known per se, such as impregnation, mixing of powders and others.

The amount of cocatalyst, when it is present, may vary from 1% to 10% by weight, preferably from 1% to 5% by weight. The cocatalyst may be added to the catalyst by processes known per se, such as adsorption from an aqueous or organic solution, followed by the evaporation of the solvent. A preferred catalyst is pure chromium oxide with nickel or zinc as cocatalyst. Alternatively, the cocatalyst may be physically mixed with the catalyst by grinding, in order to produce a fine mixture.

Another preferred catalyst is a mixed chromium/nickel catalyst supported on fluorinated alumina. The document U.S. Pat. No. 5,731,481 describes a process for the preparation of this other catalyst.

Before activation, the catalyst is subjected to a step of drying, preferably with a drying gas, such as nitrogen. The drying step may be carried out at a pressure ranging from atmospheric pressure to 20 bar. The temperature of the catalyst during the drying step may range from 20° C. to 400° C., preferably from 100° C. to 200° C.

The activation of the catalyst may preferably be carried out with HF or a fluoro- or hydrofluoroalkane and/or an oxidizing agent (preferably oxygen or chlorine). The regeneration of the catalyst may be carried out with an oxidizing agent (preferably oxygen or chlorine) and optionally HF, in one or more steps.

In order to extend the operating time of the catalyst, it is possible to add an oxidizing agent (preferably oxygen or chlorine) during the production phase, for example in a proportion of 0.05 mol % to 15 mol %, with respect to the mixture of oxidizing agent and chlorinated compound.

The temperature during the regeneration step may be from 250° C. to 500° C. approximately and the pressure from atmospheric pressure to approximately 20 bar. When HF is used in combination with oxygen, the proportion of oxygen may vary from 2 mol % to 98 mol %, with respect to the HF/oxygen mixture.

Generally, and irrespective of the envisaged reaction, it is preferred for the mean temperature difference between the reaction phase and the regeneration phase to be less than 150° C., or less than 100° C., or even less than or equal to 75° C. or 50° C. In this way, the productivity is improved by more rapidly reaching the equilibrium conditions and by limiting the side reactions at the start of the reaction phase.

It is possible to provide an intermediate purge phase between the reaction phase and the regeneration phase, and/or between the regeneration phase and the reaction phase, for example by sparging the reaction chamber 1 with nitrogen or steam (either in the direction of the reaction stream, or in the direction of the regeneration stream). Such a purge phase may however be pointless if oxygen is present anyway in the reaction stream. The use of a steam purge before the reaction phase may make it possible to preheat the reactor, due to the exothermic water adsorption on the catalyst (water being produced anyway within the context of the dehydration reactions). The adsorption of steam on an anhydrous catalyst releases a significant amount of heat (especially in the case of zeolites), which helps to significantly raise the temperature of the solid. After this initial phase, the temperature of the solid returns to normal, and it is desirable to wait for this return before injecting the reactants in order to avoid any runaway of the reaction.

In one preferred embodiment, at the end of a reaction cycle, the reactor is purged either in the direction of the reaction stream or in the opposite direction with an inert gas such as nitrogen, $CO_2$, combustion gases or steam. During this purge phase, of relatively short duration, the temperature of the catalyst bed is maintained at the same temperature, that is to say with in a range of plus or minus 10° C. about the temperature reached at the end of the reaction cycle.

At the end of the purge phase, the regeneration gas stream is introduced from the end opposite the reaction gas inlet. The regeneration stream contains oxygen, which is diluted in an inert gas containing nitrogen, $CO_2$ or steam. The oxygen partial pressure during the regeneration phase may be adjusted and in particular may start with a low oxygen content, of less than 20%, and preferably of less than 10%, which is then gradually increased in order to maintain the regeneration of the catalyst through the catalyst bed. In this case, the regeneration of the catalyst may be driven by the temperature of the hottest point in the reactor which is maintained at less than 500° C., and preferably less than 450° C., and more preferably still less than 400° C. The regeneration may also be driven by following the concentration of residual oxygen leaving the reactor and by ensuring that the conversion of the oxygen remains less than 95%, and preferably less than 90%.

At the end of the regeneration phase, a rapid purge of the reaction is carried out, while ensuring that the temperature of the catalyst bed remains within a range compatible with the start of a reaction phase after the end of the combustion of the coke. The purge may be carried out with a gas containing, for example, nitrogen, $CO_2$, combustion gases or steam. Preferably, the purge is carried out in the direction of the reaction gases.

In the case of reactions involving HF, the purges are preferably carried out in the absence of steam in order to limit the risks of corrosion.

The advantages of the invention are now illustrated non-limitingly for a process for the dehydration of glycerol to give acrolein.

EXAMPLES

Example 1

According to the Invention

A reaction tube (1) made of 316L stainless steel, having an internal diameter of 22 mm and a height of 1 m is submerged vertically in a salt bath ($KNO_3$, $NaNO_3$, $NaNO_2$ eutectic mixture) provided with a resistance heater and agitated by nitrogen bubbling. This device makes it possible to efficiently carry out the heat exchanges with the reactor. The temperature inside the reactor is monitored by 14 thermocouples located in a thermocouple sheath having an external diameter of 4 mm positioned in the center of the reaction tube. The reaction tube is charged with 0.337 liters of a $PW/TiO_2$ catalyst, prepared according to example 1 of patent application WO 2013/18915.

In a reaction phase, a positive displacement pump and 2 mass flow regulators make it possible to respectively send a mixture of glycerol/water, nitrogen and air via a line (5) into an electrically heated vaporizer electrically connected to the end (2) of the reactor located at the top thereof. The end (3) of the reactor located at the bottom thereof is connected to an automatic valve controlled by a pressure sensor which makes it possible to maintain the desired pressure in the reactor. The gas stream leaving this valve may be sent for analytical purposes to a hydroextraction column. The liquid effluent thus collected at the bottom of the column over a duration of around 10 minutes may be weighed and analysed by gas chromatography.

In order to carry out a reverse-flow regeneration phase, a line (8) fed by 2 nitrogen and air mass flow regulators is installed between the automatic valve and the bottom end (3) of the reactor. A line (7) that makes it possible to discharge a gas stream is connected to the vaporizer at the line inlet (5). In the reaction phases, valves enable the lines (8) and (7) to be closed.

In the reverse-flow regeneration phases, the line (5) is closed by a valve and the automatic valve connected to the end (3) is in the closed position.

From the instant t=0 and up to t=24 h, a reaction phase is carried out by sending a continuous stream of 675 Nl/h (normal liters per hour) of a mixture of glycerol/water/$N_2$/$O_2$ having volume ratios of 6/29/62/3 at 295° C. to the top inlet (2) of the reactor. The molten salt bath is maintained at 295° C. and the pressure of the gas stream at the outlet of the reactor is maintained at 2.3 bar absolute by the automatic valve.

From t=24 h to t=24 h 05 min, the pressure in the reactor is reduced to atmospheric pressure and the reactor is sparged by a stream of 416 Nl/h of nitrogen via the line (5). The reverse-flow regeneration phase is then started by closing the automatic valve connected to the end (3) of the reactor and the line (5) and by injecting, at atmospheric pressure, at the bottom end (3) of the reactor, via the line (8), a stream of 169 Nl/h of an air/nitrogen mixture containing 3.3% by volume of oxygen. The temperature of the molten salt is brought to 315° C. It is observed that the temperature of the catalyst bed passes through a maximum of 328° C. at the start of regeneration ("hot spot") then decreases. Starting from t=34 h, 169 Nl/h of an air/nitrogen mixture containing 7% by volume of oxygen is injected. At t=41 h 30 min, the temperature of the molten salt is reduced to 295° C.

At t=42 h, the reaction configuration is returned to by closing the lines (7) and (8). A continuous stream of 675 Nl/h (normal liters per hour) of a mixture of glycerol/water/$N_2$/$O_2$ having volume ratios of 6/29/62/3 at 295° C. is sent to the top inlet (2) of the reactor. The molten salt bath of the reactor (1) is maintained at 295° C. and the pressure of the gas stream leaving the reactor is maintained at 2.3 bar absolute by the automatic valve. Very rapidly after starting the reaction, the temperature measured in the reactor passes through a maximum of 359° C. (hot spot) before decreasing. The reaction phase is continued until t=66 h. The outgoing gas stream is sent at different moments to the hydroextraction column.

In the same way as above, a reverse-flow regeneration phase is reproduced from t=66 h to t=84 h and a reaction phase is reproduced from t=84 h to t=108 h.

Analysis of the liquid effluent resulting from the absorption column of the gas stream leaving the reactor made it possible to determine the degree of glycerol conversion and the acrolein yield, according to the following equations:

Glycerol conversion (%)=100−molar flow rate of glycerol in the gaseous effluent/molar flow rate of glycerol introduced into the reactor.

Acrolein yield (%)=molar flow rate of acrolein in the gaseous effluent/molar flow rate of glycerol introduced into the reactor.

The results are collated in table 1.

TABLE 1

| | Time (h) | Temperature of the reactor (salt bath) | Maximum hot spot | Glycerol conversion % | Acrolein yield % |
|---|---|---|---|---|---|
| Reverse-flow regeneration | 24-42 h | 315° C. | 328° C. | — | — |
| Reaction | 42 h 15-42 h 25 | 295° C. | 359° C. | >99 | 72 |
| | 65 h 30-65 h 40 | | | >99 | 70 |
| Reverse-flow regeneration | 66 h-84 h | 315° C. | 327° C. | — | — |
| Reaction | 84 h 15-84 h 25 | 295° C. | 356° C. | >99 | 72 |
| | 107 h 30-107 h 40 | | | >99 | 70 |

Example 2

Comparative

The conditions from example 1 between 0 and 24 h are reproduced.

The regeneration step is carried out from t=2 h to t=4 h without flow reversal.

From t=2 h to t=2 h 05, the pressure in the reactor is reduced to atmospheric pressure and the reactor is sparged with a stream of 416 Nl/h of nitrogen via the line (5). The regeneration phase is then started by injecting, at atmospheric pressure, a stream of 169 Nl/h of an air/nitrogen mixture containing 3.3% by volume of oxygen into the top end (2) of the reactor via the line (5). The temperature of the molten salt is brought to 315° C. It is observed that the temperature in the catalyst bed passes through a maximum of 337° C. at the start of regeneration ("hot spot") then decreases. Starting from t=3 h, 169 Nl/h of an air/nitrogen mixture containing 7% by volume of oxygen is injected. At t=4 h 30, the temperature of the molten salt is reduced to 295° C.

The conditions of example 1 between 4 h and 6 h are then reproduced. Very rapidly after starting the reaction, the temperature measured in the reactor at passes through a maximum of 378° C. (hot spot) before decreasing.

The results are collated in table 2.

TABLE 2

| | Time (h) | Temperature of the reactor (salt bath) | Maximum hot spot | Glycerol conversion % | Acrolein yield % |
|---|---|---|---|---|---|
| Regeneration without reverse flow | 24 h-42 h | 315° C. | 337° C. | — | — |
| Reaction | 42 h 15-42 h 25 | 295° C. | 378° C. | >99 | 61 |
| | 65 h 30-65 h 40 | | | >99 | 70 |

It is observed that the reverse-flow regeneration makes it possible to reduce the maximum hot spot both at the start of the reaction (328° C. and 327° C. in example 1 versus 337° C. in comparative example 2) and at the start of the regeneration (356° C. and 359° C. in example 1 versus 378° C. in comparative example 2). Furthermore, the yield 15 minutes after the start of the reaction phase is substantially improved (60% in example 1 versus 61% in comparative example 2).

The invention claimed is:

1. A chemical reaction process alternately comprising:
a reaction phase, comprising passing a reaction stream in a reaction chamber from a first end to a second end, wherein the first end is opposite the second end; and
a catalyst regeneration phase, comprising passing a regeneration stream in the reaction chamber from its second end to its first end, wherein the reaction phase does not take place simultaneously with the catalyst regeneration phase and wherein the reaction chamber comprises a plurality of separate reaction compartments, each containing a catalyst bed, and a system for heat exchange therebetween.

2. The process as claimed in claim 1, wherein the regeneration stream comprises oxygen, and the catalyst regeneration phase further comprises combusting coke deposited on the catalyst.

3. The process as claimed in claim 1, which is:
a process for the dehydration of glycerol to give acrolein; or
a process for the dehydration of lactic acid or ammonium lactate to give acrylic acid; or
a process for the dehydration of 3-hydroxypropionic acid or the ammonium salt thereof to give acrylic acid; or
a process for the dehydration of 2-hydroxyisobutyric acid or 3-hydroxyisobutyric acid or the corresponding ammonium salts thereof to give methacrylic acid; or
a process for the conversion of a chlorinated compound into a fluorinated compound, preferably a process for the preparation of a hydrofluoroolefin or of a hydrofluorocarbon, in particular a process for the preparation of a fluoropropene and very particularly preferably a process for the preparation of 2,3,3,3-tetrafluoropropene; or
a selective oxidation process such as the oxidation of methanol to give formaldehyde or dimethoxymethane; the oxidation of ethanol to give acetaldehyde or diethoxyethane; the oxidation of ortho-xylene or naphthalene to give phthalic anhydride; the oxidation of benzene, butene, butanol or butane to give maleic anhydride; the oxidation of propylene to give acrolein; or the oxidation of isobutene or tert-butanol to give methacrolein.

4. The process as claimed in claim 1, wherein the reaction phase has a duration of greater than or equal to 15 minutes and/or the regeneration phase has a duration of greater than or equal to 15 minutes.

5. The process as claimed in claim 1, wherein the reaction phase and the regeneration phase have predetermined durations; or wherein the duration of the reaction phase and/or the duration of the regeneration phase depend on the measurement of a parameter such as a temperature in the reactor or the content of a compound in a stream leaving the reactor.

6. The process of claim 1, wherein the process takes place in a chemical reactor, the reactor comprising:
a reaction chamber comprising a catalyst bed, the reaction chamber comprising a first end and a second end opposite the first end;
a reaction stream supply pipe connected to an inlet of the reaction chamber at its first end;
a reaction stream withdrawal pipe connected to an outlet of the reaction chamber at its second end;
a regeneration stream supply pipe connected to an inlet of the reaction chamber at its second end;
a regeneration stream withdrawal pipe connected to an outlet of the reaction chamber at its first end; and
a switching mechanism adapted to alternately allow the passage of a reaction stream in the reaction chamber from the reaction stream supply pipe to the reaction stream withdrawal pipe, and the passage of a regeneration stream from the regeneration stream supply pipe to the regeneration stream withdrawal pipe.

7. The process of claim 6, wherein the reactor comprises a plate reactor or a multitubular reactor.

8. The process of claim 3, wherein the selective oxidation process is selected from the group consisting of the oxidation of methanol to give formaldehyde or dimethoxymethane; the oxidation of ethanol to give acetaldehyde or diethoxyethane; the oxidation of ortho-xylene or naphthalene to give phthalic anhydride; the oxidation of benzene, butene, butanol or butane to give maleic anhydride; the oxidation of propylene to give acrolein; and the oxidation of isobutene or tert-butanol to give methacrolein.

9. The process of claim 3, wherein the conversion of a chlorinated compound into a fluorinated compound comprises a process for the preparation of a hydrofluoroolefin or a hydrofluorocarbon.

10. The process of claim 9, wherein the process for the preparation of a hydrofluoroolefin or a hydrofluorocarbon comprises a process for the preparation of a fluoropropene.

11. The process of claim 10, wherein the fluoropropene is 2,3,3,3-tetrafluoropropene.

* * * * *